United States Patent
Lopatin et al.

(10) Patent No.: US 9,121,814 B2
(45) Date of Patent: Sep. 1, 2015

(54) METHOD AND APPARATUS FOR DETERMINING A FRACTION OF AN ADSORBED MATERIAL CONTAINED IN AN ADSORBER MATERIAL

(75) Inventors: Sergej Lopatin, Lorrach (DE); Thomas Uehlin, Schopfheim (DE)

(73) Assignee: ENDRESS + HAUSER GMBH + CO. KG, Maulburg (DE)

( * ) Notice: Subject to any disclaimer, the term of this patent is extended or adjusted under 35 U.S.C. 154(b) by 171 days.

(21) Appl. No.: 13/637,700

(22) PCT Filed: Feb. 28, 2011

(86) PCT No.: PCT/EP2011/052913
§ 371 (c)(1),
(2), (4) Date: Sep. 27, 2012

(87) PCT Pub. No.: WO2011/124419
PCT Pub. Date: Oct. 13, 2011

(65) Prior Publication Data
US 2013/0015864 A1    Jan. 17, 2013

(30) Foreign Application Priority Data

Apr. 8, 2010    (DE) .................... 10 2010 003 710

(51) Int. Cl.
*G01R 27/26*    (2006.01)
*G01N 19/00*    (2006.01)
(Continued)

(52) U.S. Cl.
CPC .......... *G01N 27/225* (2013.01); *B01D 53/0454* (2013.01); *B01D 53/261* (2013.01); *B01D 2253/108* (2013.01); *B01D 2257/80* (2013.01)

(58) Field of Classification Search
CPC ............. G01N 27/225; B01D 53/0454; B01D 2253/108; B01D 2257/80; B01D 53/261

USPC ....................... 324/663; 73/335.03
See application file for complete search history.

(56) References Cited

U.S. PATENT DOCUMENTS 3,186,225 A    6/1965 Freeman, Jr. et al.
3,263,492 A    8/1966 Lerner
(Continued)

FOREIGN PATENT DOCUMENTS

DE    38 02 751 A1    8/1989
DE    197 17 711 A1    10/1998
(Continued)

OTHER PUBLICATIONS

Wang et al., "Humidity sensors based on silica nanoparticle aerogel thin films," Sensors and Actuators B, Elsevier Sequoia S.A., Lausanne, CH, XP025328384 (May 27, 2005), Online Dec. 15, 2004.
(Continued)

*Primary Examiner* — Melissa Koval
*Assistant Examiner* — Farhana Hoque
(74) *Attorney, Agent, or Firm* — Bacon & Thomas, PLLC

(57) ABSTRACT

A method for determining a fraction of an adsorbed material contained in a formed body serving as an adsorber material. For the case in which the adsorber material is present in the form of a formed body, at least two electrodes are arranged, spaced apart from one another, on a surface of the formed body and/or are firmly inserted in the formed body; that, for the case, in which the adsorber material is present in the form of a powder or granulate, a corresponding formed body made of the same material is durably inserted in the powder or granular material. The electrodes are supplied with an alternating electrical current, whereby an electrical characteristic variable is ascertained; and, based on the characteristic variable, degree of saturation of the adsorber material is ascertained. Furthermore, a corresponding apparatus is claimed.

11 Claims, 6 Drawing Sheets

(51) Int. Cl.
    *G01N 27/22*     (2006.01)
    *B01D 53/04*     (2006.01)
    *B01D 53/26*     (2006.01)

(56) References Cited

U.S. PATENT DOCUMENTS

| | | | | |
|---|---|---|---|---|
| 3,920,189 A | * | 11/1975 | Maggiacomo et al. | 239/526 |
| 4,546,442 A | | 10/1985 | Tinker | |
| 4,860,584 A | | 8/1989 | Mercer et al. | |
| 4,876,890 A | * | 10/1989 | Mercer et al. | 73/335.03 |
| 5,260,667 A | * | 11/1993 | Garcia-Golding et al. | 324/694 |
| 2002/0021117 A1 | * | 2/2002 | Puskas et al. | 324/71.1 |
| 2009/0261987 A1 | | 10/2009 | Sun | |
| 2010/0234983 A1 | * | 9/2010 | Gesuita et al. | 700/217 |

FOREIGN PATENT DOCUMENTS

RU     2225087 C2     3/2004
WO    01/90732 A2     11/2001

OTHER PUBLICATIONS

International Search Report in PCT/EP2011/052913.
German Search Report in 10 2010 003 710.9, dated Aug. 4, 2010.

* cited by examiner

METHOD AND APPARATUS FOR DETERMINING A FRACTION OF AN ADSORBED MATERIAL CONTAINED IN AN ADSORBER MATERIAL

TECHNICAL FIELD

The present invention relates to a method for determining a fraction of an adsorbed material, which is contained in a formed body, granular material or powder of zeolite, a zeolite composition or silica gel serving as an adsorber material. Furthermore, the invention relates to a corresponding apparatus. The adsorbed material is, for example, water or a gas.

BACKGROUND DISCUSSION

In order to keep a material away from an element located in an essentially closed volume, wherein this element could be damaged by this material, it is known to introduce into the volume an adsorber in the form of a solid or granular material, wherein the adsorber collects the material, and thus keeps it away from the element. For example, electronic components are sensitive to humidity, which condenses out. A hygroscopic insert, which is arranged in the immediate vicinity of the component in a shared housing, withdraws the moisture from the air, whereby the condensing out is prevented. Known adsorbers include, for example, zeolite and silica gel. The collecting ability of an adsorber is, however, limited, so that knowledge concerning the degree of saturation is desirable.

For determining the water content in a bulk good, from DE 19717711 A1, a measuring cell with two electrodes separated from one another via an intermediate space is known. In the case of introduction of the measuring cell into the bulk good, the intermediate space is filled with the bulk good, so that via a subsequent measuring of conductivity, the moisture content of the bulk good can be determined. A disadvantage in the case of this method is that the quality of the measuring depends on how homogeneously the hollow space is filled with the bulk good. This method is not suitable for determining content of a gas.

Known from DD 135241 is a measurement capacitor for determining the moisture content in the interior of a solid. Bores are made in the solid substance, and, when required, the measurement capacitor is inserted into the bores. For the measuring, the electrodes of the measuring capacitor are pressed onto the wall of the bore, supplied with a high-frequency alternating voltage, and the capacitance is measured, and therefrom, the moisture content is determined. A disadvantage of the invention is that the dimensions of the measuring capacitor and the bores must be matched to one another. In the case of solids of smaller dimensions or of special form, measurement is not possible.

SUMMARY OF THE INVENTION

An object of the invention is to provide an easy method and corresponding apparatus, with which a material is adsorbable from the environment via a zeolite, a zeolite composition or a silica gel serving as an adsorber material, and, moreover, wherein the fraction of the adsorbed material contained in the adsorber material can be determined.

The object is achieved by a method wherein, for the case, in which the adsorber material is present in the form of a formed body, at least two electrodes are applied, spaced apart from one another, on a surface of the formed body and/or are firmly inserted in the formed body; for the case, in which the adsorber material is present in the form of a powder or granulate, a formed body is produced from the same material, at least two electrodes are applied, spaced apart from one another, on a surface of the formed body, and/or are firmly inserted in the formed body, and the formed body is durably inserted in the powder or granular material; the electrodes are supplied with an alternating electrical current, whereby the capacitance and/or the loss factor tan $\delta$ is ascertained as the electrical characteristic variable of the adsorber material; and, based on the ascertained electrical characteristic variable, the fraction of the adsorbed material in the adsorber material and the degree of saturation of the adsorber material is ascertained.

The two electrodes are, in such case, arranged in such a manner that they form a capacitor. This serves for ascertaining the electrical characteristic variable, which is dependent on the fraction of the adsorbed material contained in the adsorber material and has a unique relationship with such fraction. In this way, information can be obtained concerning the amount of adsorbed material already collected. In the case of known maximum saturation of the adsorber material, its remaining loading capacity for the material to be adsorbed is thus additionally determinable. Via continuous measuring, or measurements repeated in short intervals, the degree of saturation of the adsorber material can be monitored. The adsorbed materials include, for example, water or polar, gaseous molecules.

The method includes the feature that capacitance or the loss factor tan $\delta$ serves as an electrical characteristic variable. It is likewise possible to ascertain both the capacitance as well as also the loss factor, especially when two different materials are adsorbed, and their respective fractions are to be determined. The loss factor tan $\delta$ of the loss angle $\delta$ refers in such case to the ratio of resistive power to reactive power, and is independent of the geometry of the electrodes and of the body in and/or on which these are arranged. The loss factor tan $\delta$ can be determined from the phase shift $\phi$ between electrical current and voltage of the test capacitor, i.e. the electrodes supplied with the alternating voltage, in the following way:

$$\tan \delta = \tan(\pi/2 - \phi).$$

From the loss factor tan $\delta$, the degree of saturation $\alpha$ of the adsorber material is directly determinable. Similarly, in the case of capacitance measurement, the dielectric constant is a measure for the degree of saturation. The dielectric constant and therewith the capacitance, as well as the loss factor are also influenced to different degrees by different adsorbed materials, because of their different degrees of polarity.

In an additional embodiment, the electrodes are supplied with an alternating electrical current with a frequency of between 1 and 100 kHz. Especially for zeolite as an adsorber material, this range is especially advantageous, since the loss factor tan $\delta$ of saturated zeolites in this frequency range is almost independent of the measuring frequency, and thus a stable measuring is assured.

In an advantageous embodiment, the formed body, which is inserted in the granular material or the powder, is produced in a sinter method, a press method and/or a CIM (Ceramic Injection Molding) method. If the adsorber material is zeolite, the formed body is preferably manufactured from a mixture of a zeolite with a binding agent.

The object as concerns an apparatus for adsorption of at least one material from the environment—such apparatus containing a formed body, a granular material or a powder of zeolite, a zeolite composition or silica gel serving as an adsorber material, and such apparatus serving for determining the fraction of adsorbed material contained in the adsorber material—is achieved by features including that, in the case, in which the adsorber material is present as a formed body, at least two electrodes are applied, spaced apart from one another, on a surface of the formed body, and/or are firmly inserted in the formed body; that, in the case, in which the adsorber material is present in the form of powder or granular material, a formed body made of the same material is durably inserted into the powder or granular material; wherein at least two electrodes are applied, spaced apart from one another, on a surface of the formed body and/or are durably inserted in the formed body; that associated with the apparatus is an electronics unit, which supplies the electrodes with an alternating electrical current and therewith ascertains the capacitance and/or the loss factor tan δ as the electrical characteristic variable of the adsorber material; and that the electronics unit, based on the ascertained electrical characteristic variable, determines the fraction of adsorbed material contained in the adsorber material and the degree of saturation of the adsorber material. In other words, based on the electrical characteristic variable, the degree of conversion α, or the degree of saturation, of the adsorber material is determinable.

The apparatus of the invention thus enables, in addition to the collecting of the material to be adsorbed, also a state diagnosis, and therewith development of information concerning the remaining lifetime as an adsorber. This is of great importance especially in the case of use of the apparatus in connection with predictive maintenance for protection of elements of a process device against deposition of the material to be adsorbed. Due to the early warning, the apparatus can be replaced by a new apparatus before the adsorber material is completely saturated, whereupon protection against the adsorbed material would no longer be assured.

In an embodiment, the adsorber material is a zeolite or a composition composed of a zeolite and a binding agent. The formed body is correspondingly a zeolite ceramic body, or a ceramic body produced from a composition of zeolite and a binding agent, wherein the binding agent is a clay-like substance. Zeolite possesses a crystal structure with relatively large hollow spaces and channels, into which molecules of corresponding size can penetrate and be adsorbed. Especially strongly polar molecules are adsorbed by zeolite, since such molecules form a stable bond with oxygen atoms in the zeolite. Water molecules are an example of this. For this reason, zeolite is especially suitable for adsorption of moisture. The determining, according to the invention, of the contained fraction of one or more adsorbed materials exploits the fact that the adsorbed materials change the material properties of the basic material.

In an additional embodiment of the invention, the measuring cell is manufactured in such a manner that the material of the measuring cell has pores. The pores favor the access and the adsorption of gaseous materials.

In a preferred embodiment of the invention, the formed body composed of the adsorber material is produced in a sintering method and/or a press method or a CIM (Ceramic Injection Molding) method. Via these methods, bodies of any form as well as a desired, predetermined density can be produced from powdered materials.

In an additional embodiment, the formed body is disc shaped, ring shaped, prismatic or cylindrical. It can, in such case, equally be a solid body or hollow body.

In a further development of the measuring cell of the invention, the electrodes are applied in the form a flat or strip shaped coating on the surface of the formed body.

In an additional embodiment of the invention, the adsorbed material is water, ammonia, hydrogen sulfide, carbon dioxide, ozone and/or hydrogen fluoride.

In an embodiment, the apparatus of the invention is used for determining or monitoring degree of saturation of the adsorber material located in a container in the form of a granular material or powder. For example, a storage container is involved, in which the adsorber material is located as raw material before its further processing. The introduction of an apparatus, which monitors the degree of saturation of the adsorber material with the material to be adsorbed before the processing, assures a sufficient adsorption capability of the end product.

In an additional embodiment, the apparatus of the invention is used as a replaceable insert for collecting moisture in a process device. In EP 01464923 A1, the problem of condensation of humidity in the interior of a housing of a process device for flow measurement is described. The solution proposed there includes monitoring the relative humidity and temperature in the interior of the housing, and checking their movement as a function of time, so that an imminent condensation is recognizable, and a warning can be output. Since the housing is, in the normal case, embodied in an air tight manner, such a warning is, as a rule, associated with an unsealed location in the housing. This can be detected and sealed, or the measurement transducer can be replaced, before a condensate deposited on the electronics can lead to its failure. An apparatus of the invention installed in the interior of the housing of such a process device presents an improved alternative. The adsorber material adsorbs moisture penetrating into the housing up until the point that becomes saturated. By determining the degree of saturation by means of the inserted or applied electrodes, a warning can be produced when the adsorber material has reached a certain degree of saturation and needs to be replaced.

BRIEF DESCRIPTION OF THE DRAWINGS

The invention will now be explained in greater detail based on the appended drawing, the figures of which show as follows:

FIG. 4c is schematically in section, a contacting variant for an arrangement according to FIG. 4a;

DETAILED DISSCUSSION IN CONJUNCTION WITH THE DRAWINGS

Figure 1:
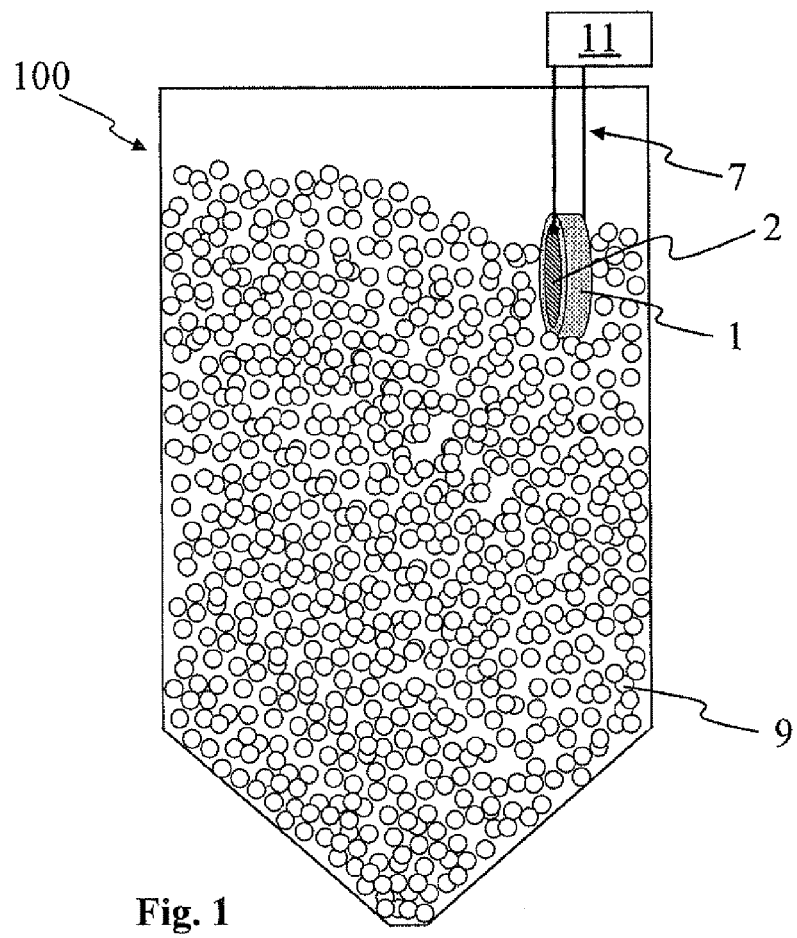
FIG. 1 is a first example of use of an apparatus of the invention.

FIG. 1 illustrates an example of application for an apparatus of the invention. The formed body 1, which is composed of the adsorber material and equipped with electrodes 2, is inserted in a storage container 100, in which is located a granular material 9 likewise composed of the adsorber material. Such storage containers 100 are required, for example, in the manufacture of desiccant cartridges, which contain metered quantities of granular material 9 of moisture adsorbing material. The desiccant cartridges are versatilely applicable anywhere where a bounded region must be protected against moisture. Since the moisture adsorption is a property inherent to the adsorber material, the danger exists that the adsorber material will collect moisture while in storage container 100, if moisture has penetrated into storage container 100. A drying cartridge manufactured of this granular material 9 would have a shortened lifetime corresponding to the amount of moisture already collected. Formed body 1 composed of the same material and inserted with the granular material 9 into storage container 100, likewise adsorbs the moisture. By determining an electrical characteristic variable dependent on moisture content by means of electrodes 2 connected via electrical lines 7 with an electronics unit 11 and arranged on and/or in formed body 1, the moisture content of the adsorber material is determinable for formed body 1 and thus also for the granular material 9. This enables monitoring the degree of saturation of the granulate 8, so that it is assured that drying cartridges are produced with a sufficient loading capacity. Preferably, the determining of the moisture dependent electrical characteristic variable of the adsorber material occurs automatically at certain time intervals. If a critical moisture content is exceeded, an alarm signal is produced and, in given cases, the metered dispensing of the adsorber material is stopped.

Figure 2:
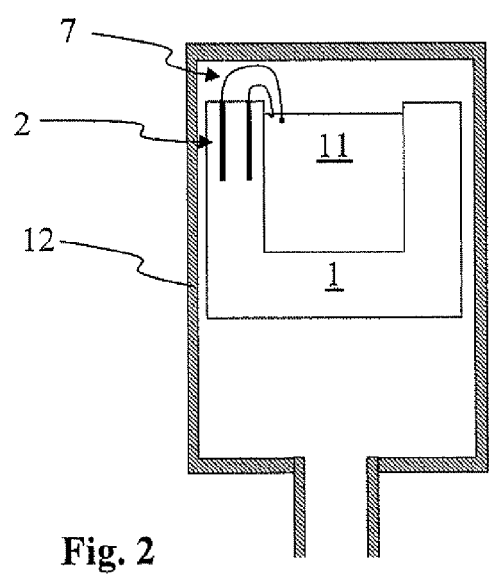
FIG. 2 is a second example of use of an apparatus of the invention.

FIG. 2 shows a further example of use of the apparatus of the invention. In such case, the apparatus, which comprises a formed body 1 or a container 10, which is filled with granular material 9 and which is permeable for the material to be adsorbed and into which a formed body 1 is inserted, is inserted into the sensor housing 12 of a process device and is arranged in such a manner so as to be replaceable. The selected adsorber material of the apparatus adsorbs a material, which, in the case of its penetration into the sensor housing 12 and following deposition on device parts, would lead to problems. For example, a sensor electronics 11 arranged in sensor housing 12 is to be protected against moisture deposition, since this can bring about short circuits, which result in a malfunctioning or even to failure of the process device. A simple drying cartridge protects sensor electronics 11 against moisture only over a certain period of time, since the adsorber material possesses a limited moisture collecting ability. If the adsorber material becomes saturated, protection of sensor electronics 11 is no longer assured. The apparatus of the invention includes, consequently, electrodes 2, which are inserted in the adsorber material, for example, a zeolite. Preferably, these electrodes 2 are connected via electrical lines with sensor electronics 11, which supplies the electrodes 2 with an alternating electrical current, and ascertains an electrical characteristic variable, for example, the loss factor. Alternatively, electrodes 2 are associated with a separate electronics unit. From the electrical characteristic variable, the degree of saturation of the adsorber material is ascertainable. Preferably, the degree of saturation is regularly determined, and an alarm signal is produced when a certain degree of saturation, for example, 90%, is reached. This alarm signal signals, for example to a control room, that replacement of the adsorber material is required. If a corresponding replacement occurs, it is assured that the element to be protected continues to be protected, and that the process device delivers reliable results without gaps. Collected moisture can be withdrawn from zeolites via heating, so that they may be useable again as drying cartridges.

Figure 3:
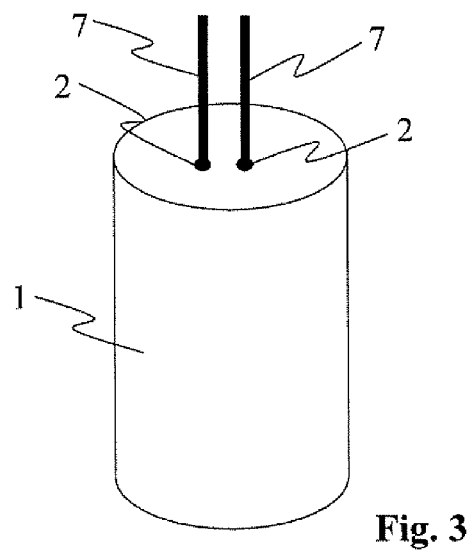
FIG. 3 is schematically, a solid cylinder composed of the adsorber material, with electrodes inserted.

FIG. 3 shows a first variant for arrangement of the electrodes 2 using the example of a formed body 1 of cylindrical shape, composed of a zeolite composition. The measuring of the electrical characteristic variable occurs directly in formed body 1. For this, the electrodes 2 are inserted into formed body 1, for example, in the form of metallized bores, and are connected with electrical lines 7, via which they are contactable with an electrical signal.

Figure 4A:
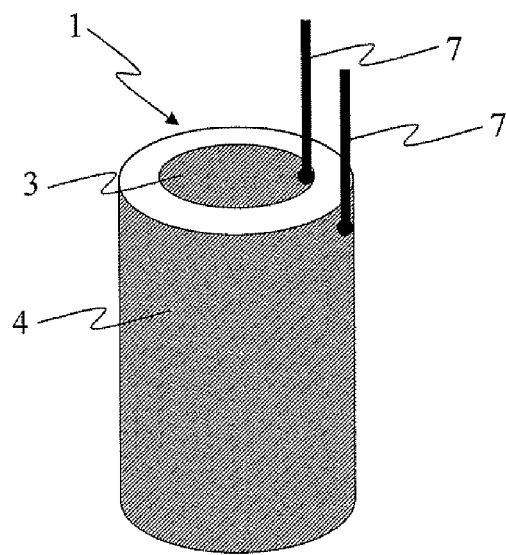
FIG. 4a is schematically, a hollow cylinder composed of the adsorber material with a first flat electrode arrangement.
Figure 4B:
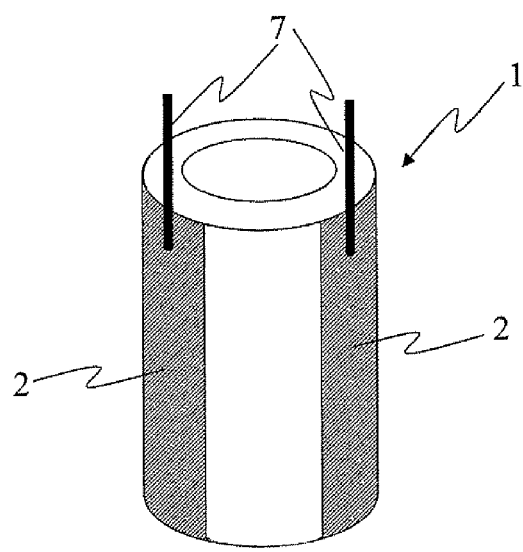
FIG. 4b is schematically, a hollow cylinder composed of the adsorber material with a second flat electrode arrangement.
Figure 4C:
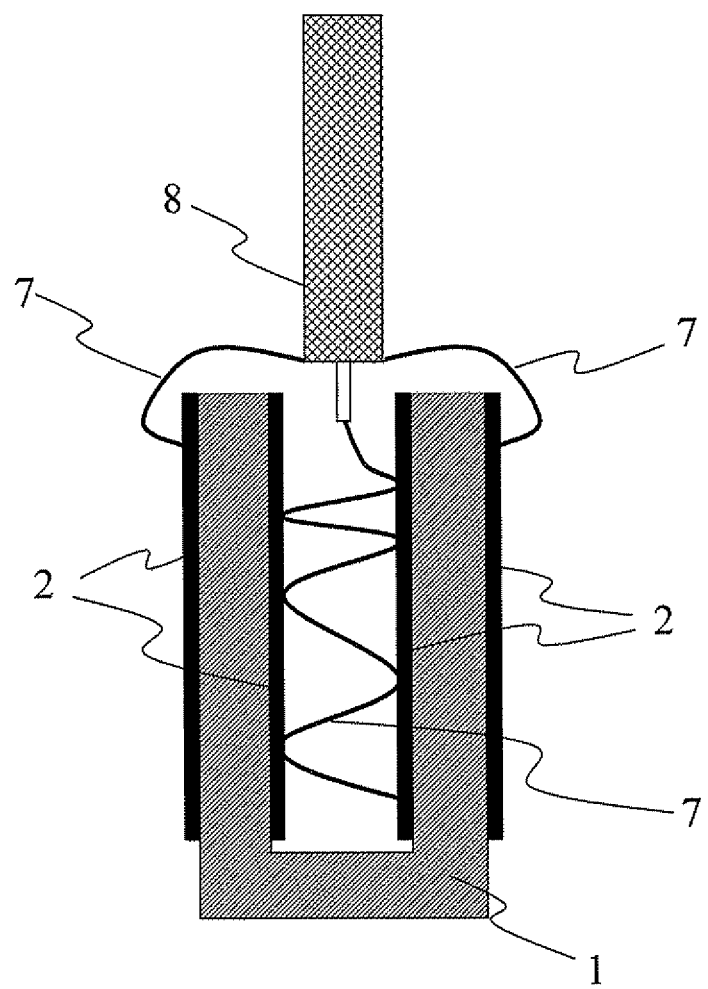

FIGS. 4*a*-*c* disclose advantageous embodiments of electrodes with corresponding electrical contacting, wherein the electrodes 2 are in each case applied on the surface of formed body 1, depicted as a hollow cylinder. In FIG. 4*a*, the outer surface 4 and the inner surface 3 of the hollow cylinder are provided with an electrically conductive coating, while the annular upper side and underside are in each case free of the coating, so that outer surface 4 is electrically insulated from inner surface 3. The coating is preferably made of silver, gold, platinum or nickel. Any metal with good conductivity is suitable. Outer surface 4 and inner surface 3 are in each case contacted by an electrical line 7, for example, a wire. In the case of the variant illustrated in FIG. 4*b*, two electrodes 2 are applied in the form of strip shaped coatings on the outer surface 4 of formed body 1, and are contacted by electrical lines 7. The relative arrangement of the two strips to one another can in such case be selected as desired. Although the strip in this embodiment has the same length as the cylinder, this need not absolutely be the case; strips with smaller dimensions are equally suitable. FIG. 4*c* shows an advantageous embodiment of the contacting in the case of an electrode arrangement according to FIG. 4*a*. For this, a coaxial cable 8 is bared of insulation in an end region and the line is connected with the coating of inner surface 3, while the shield contacts the coated outer surface 9.

The preferred forms of embodiment illustrated in FIG. 3 and FIGS. 4*a*-*c*, can, in each case, also be components of a larger formed body 1 of more complex structure. Especially in the case of arrangement of such an apparatus in a process device, the shape and size of the formed body 1 are advantageously designed corresponding to the architecture of the process device and the region to be protected by the apparatus against the material to be adsorbed.

Figure 5:
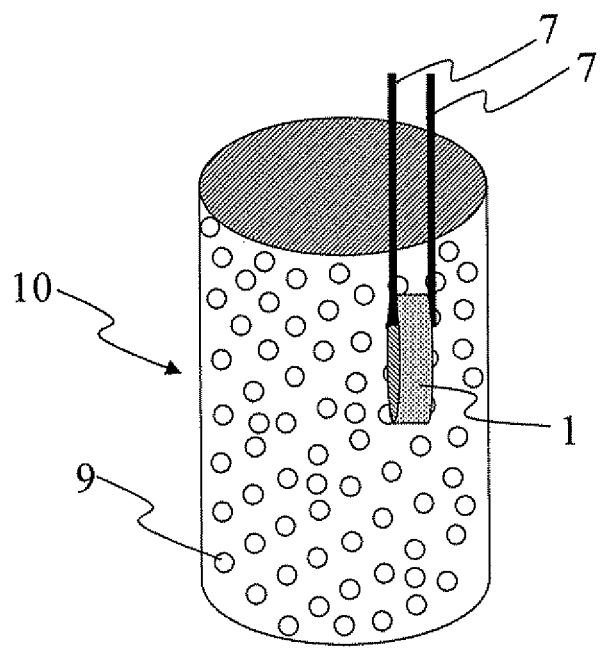
FIG. 5 is schematically, a container with a granular adsorber material, and an inserted, disk shaped, formed body.

FIG. 5 shows a container 10, in which the adsorber material is contained as a granular material 9, e.g. in the form of small, sintered, zeolite balls. The wall of the container is preferably permeable for the material to be adsorbed. For example, container 10 is a compact insert for insertion in the housing 12 of a process device. Especially, container 10 is a drying cartridge. In order to determine the degree of saturation of the granulate 9, a formed body 1 made of the same adsorber material is inserted into the container 10, wherein this formed body 1 is provided with electrodes 2 and is connectable to an electronics unit.

Figure 5A:
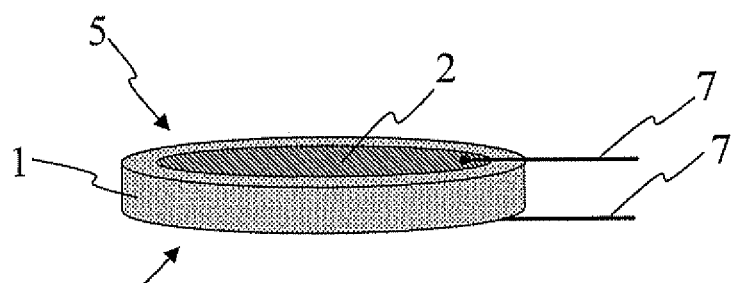
FIG. 5a is schematically, a disk shaped formed body with a first electrode arrangement.
Figure 5B:
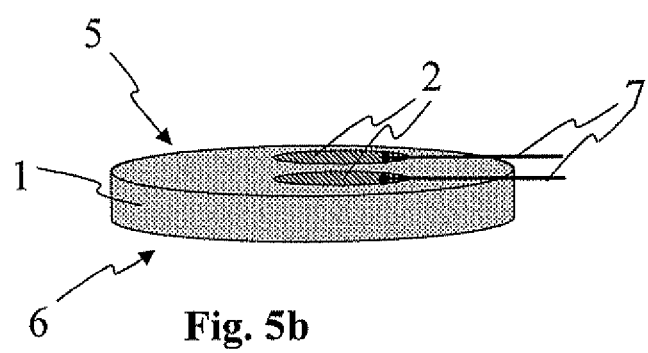
FIG. 5b is schematically, a disk shaped formed body with a second electrode arrangement.

FIGS. 5*a* and 5*b* show preferred embodiments of a disk shaped, formed body 1 for insertion into a granular material 9 or powder. Of course, the disk shape is not limited to use in a granular material 9. FIG. 5*a* shows a ceramic formed body 1 composed of the adsorber material, in the case of which the circular upper side 5 and underside 6 are in each case provided with a coating, which forms the electrodes 2 and is contacted by electrical lines 7. The coating is applied evenly. Other embodiments are, however, options, in the case of which the coating covers an annular area. An alternative electrode arrangement is shown FIG. 5*b*. There, the circular upper side 5 of the formed body 1 has a coating in the form of two strips, while the underside 6 is free of coating. The supply lines 7 for contacting are correspondingly located on only one side of formed body 1.

Figure 6:
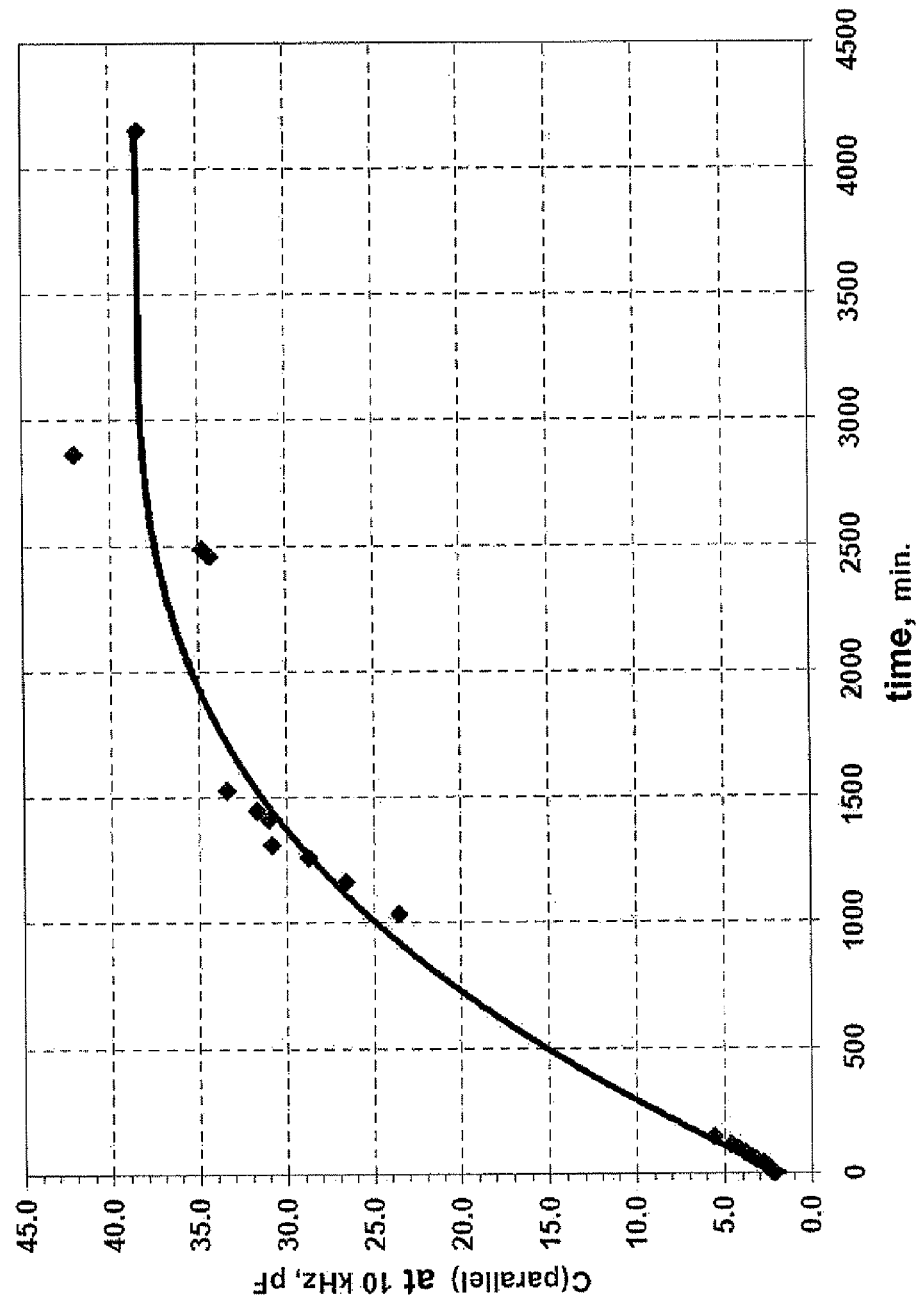
FIG. 6 is a graph of capacitance as a function of the saturation.
Figure 7:
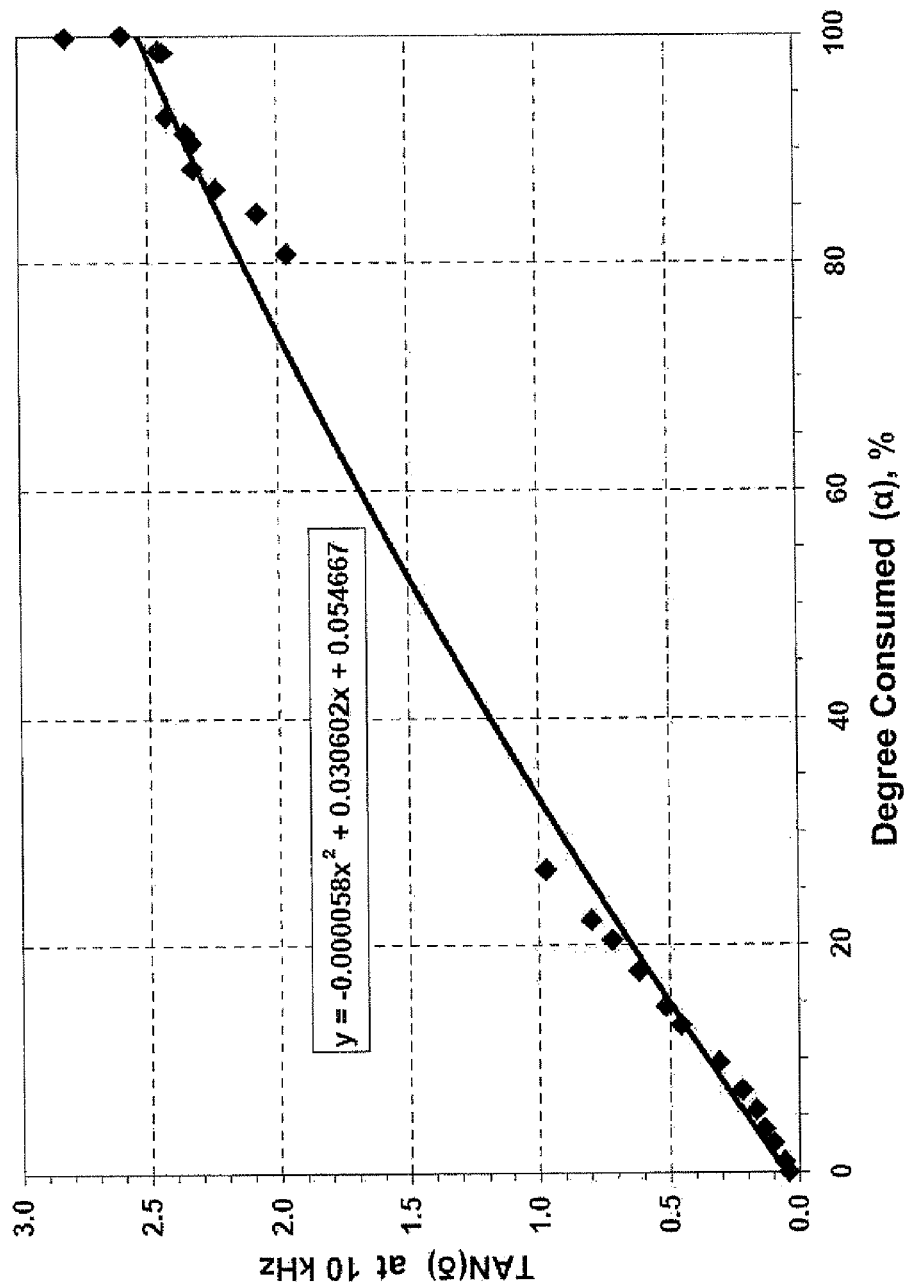
FIG. 7 is a graph of loss factor as a function of saturation.

The measuring of the fraction of adsorbed material contained in the adsorber material is explained based on FIGS. 6 and 7 using the example of zeolite as an adsorber material and water as the adsorbed material. In principle, such characteristic lines are, however, also recordable for other adsorber materials and adsorbed materials. These differentiate themselves from one another, for example, in their slopes. FIG. 6 and FIG. 7 show characteristic lines, which were recorded with an apparatus according to FIG. 5*b* using a sintered zeolite body. For this, the apparatus was inserted in a chamber with 75% relative humidity and a temperature of 25° C.

FIG. 6 shows the result of a capacitance measurement, wherein, in intervals of time, the capacitance of the capacitor formed by the two strip electrodes was determined in the case of the electrodes being supplied with an alternating electrical current of 10 kHz frequency. The capacitance rises with increasing moisture content of the zeolite, and after about 3000 min, reaches a limit value, since the zeolite after this amount of time is saturated with moisture.

FIG. 7 shows the characteristic line of the loss factor tan 5 as a function of the degree consumed α, wherein a degree consumed of 100% corresponds to complete saturation of the zeolite with moisture. The characteristic line was likewise recorded in the case of a supplying of the electrodes with an alternating electrical current of 10 kHz frequency. The loss factor is a material parameter and is independent of the geometry of the body, with which the measuring occurs, so that the determining of this measured variable is especially advantageous. As already mentioned, the loss factor is determinable from the phase shift between electrical current and voltage of the capacitor. As is to be gathered from the appearance of the characteristic line, there exists between the loss factor tan $\delta$ and the degree consumed a an approximately linear relationship across the entire range. The moisture content of the zeolite is, consequently, uniquely determinable from the loss factor.

The invention claimed is:

1. A method for determining a fraction of an adsorbed material, which is located in a container in the form of a granular material or powder of zeolite, a zeolite composition or silica gel serving as adsorber material, comprising the steps of:
producing a formed body from the same material as the adsorber material and providing, at least two electrodes which form a capacitor, spaced apart from one another, on a surface of the formed body and/or firmly inserted in the formed body, and the formed body is durably inserted in the powder or granular material;
supplying the electrodes with an alternating electrical current, whereby capacitance and/or loss factor tan $\delta$ are/is ascertained as the electrical characteristic variable of the adsorber material; and
based on the ascertained electrical characteristic variable, the fraction of the adsorbed material in the adsorber material and degree of saturation of the adsorber material is ascertained.

2. The method as claimed in claim 1, wherein:
the electrodes are supplied with an alternating electrical current with a frequency of between 1 and 100 kHz.

3. The method as claimed in claim 1, wherein:
the formed body, which is inserted in the granular material or the powder, is produced according to one of: in a sinter method, a press method and/or a CIM method.

4. An apparatus for adsorption of at least one material from the environment comprising:
a granular material or a powder of zeolite, a zeolite composition or silica gel serving as an adsorber material and for determining the fraction of the adsorbed material contained in the adsorber material;
a formed body made of the same material as the adsorber material is durably inserted in the powder or granular material, and
at least two electrodes disposed on a surface of the formed body and/or firmly inserted in formed body wherein the two electrodes form a capacitor; and
an electronics unit, which supplies said electrodes with an alternating electrical current, and therewith ascertains capacitance and/or loss factor tan $\delta$ as an electrical characteristic variable of said adsorber material, wherein:
said electronics unit, based on the ascertained electrical characteristic variable, determines the fraction of adsorbed material contained in said adsorber material and the degree of saturation of said adsorber material.

5. The apparatus as claimed in claim 4, wherein:
the adsorber material has pores.

6. The apparatus as claimed in claim 4, wherein:
said formed body composed of the adsorber material is produced in a sintering method and/or a press method or a CIM method.

7. The apparatus as claimed in claim 6, wherein:
said formed body is essentially disc shaped, ring shaped, prismatic or cylindrical.

8. The apparatus as claimed in claim 4, wherein:
said electrodes are applied in the form of a flat or strip shaped coating on the surface of said formed body.

9. The apparatus as claimed in claim 4, wherein:
the adsorbed material is water, ammonia, hydrogen sulfide, carbon dioxide, ozone and/or hydrogen fluoride.

10. The use of an apparatus as claimed in claim 4 for determining or monitoring degree of saturation of said adsorber material, located in a container in the form of a granular material or powder.

11. The use of an apparatus as claimed in claim 4 as a replaceable insert for collecting moisture in a process device.

\* \* \* \* \*